United States Patent [19]

Schneider et al.

[11] Patent Number: 5,780,445
[45] Date of Patent: Jul. 14, 1998

[54] TOCOPHERYL GLYCOSIDES, THEIR PREPARATION, AND THEIR USE AS SURFACTANTS, AS ANTIOXIDANTS AND AS THE ACTIVE SUBSTANCE PREVENTING CELL AGEING IN COSMETIC OR PHARMACEUTICAL PREPARATIONS

[75] Inventors: Günther Schneider; Joachim Thiem; Martina Lahmann, all of Hamburg, Germany

[73] Assignee: Beiersdorf AG, Hamburg, Germany

[21] Appl. No.: 594,619

[22] Filed: Feb. 2, 1996

[30] Foreign Application Priority Data

Feb. 10, 1995 [DE] Germany ............... 195 04 398.7

[51] Int. Cl.⁶ .................................................. A61K 31/70
[52] U.S. Cl. ........................ 514/27; 514/25; 514/54
[58] Field of Search ............................ 536/9.1, 18.1, 536/123; 579/27, 25, 54

[56] References Cited

U.S. PATENT DOCUMENTS

| | | | |
|---|---|---|---|
| 4,617,292 | 10/1986 | Satoh et al. | 519/27 |
| 5,280,111 | 1/1994 | Shoji et al. | 536/4.1 |

FOREIGN PATENT DOCUMENTS

| | | |
|---|---|---|
| 0169716 | 1/1986 | European Pat. Off. |
| 0611152 | 8/1994 | European Pat. Off. |
| 4320871 | 1/1995 | Germany |

OTHER PUBLICATIONS

Chemical Abstracts, vol. 119, No. 18, (1993), abstract No. 188293a, T. Saegusa: "Preparation of Liquiritin Derivativs as Melanin Formation Inhibitors and Skin Preparations Containing Them". p. 516, & JP-A-05 140 181 (Sansei Seiyaku K.K.), (1993).

*Primary Examiner*—Elli Peselev
*Attorney, Agent, or Firm*—Sprung Kramer Schaefer & Briscoe

[57] ABSTRACT

Tocopheryl glycosides of the general formula

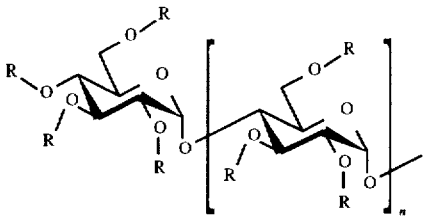

or of the general formula

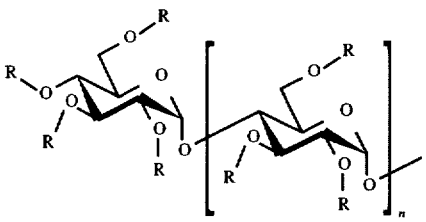

where n can adopt values of 0–6 and where R represents a radical from the group consisting of H, branched and unbranched alkyl of 1–18 carbon atoms, branched and unbranched acyl of 1–18 carbon atoms, and where R within one molecule can be identical in all positions of tie glycosyl groups, but can also adopt different meanings within one molecule, such that it is possible within one molecule to choose any desired combinations of the radicals represented.

9 Claims, No Drawings

TOCOPHERYL GLYCOSIDES, THEIR PREPARATION, AND THEIR USE AS SURFACTANTS, AS ANTIOXIDANTS AND AS THE ACTIVE SUBSTANCE PREVENTING CELL AGEING IN COSMETIC OR PHARMACEUTICAL PREPARATIONS

The present invention relates to novel active substances, to their preparation and to their use in the field of cosmetic and of pharmaceutical dermatology. The present invention relates, in particular, to active substances and to cosmetic or dermatological preparations comprising such active-substance combinations. In particular, the present invention relates to cosmetic preparations which comprise substances which protect the skin, and also the preparations themselves, against oxidation processes. The invention additionally relates to active substances which possess surfactant properties.

Stable cosmetic emulsions comprise surface-active substances, so-called surfactants or emulsifiers. These substances decrease the interfaces between the phases and form interfacial films at the oil/water phase boundary, thereby counteracting the irreversible flow merging of the dispersed phase.

Effective emulsifiers are therefore distinguished by a very good emulsifying, solubilizing and dispersing capacity. It is highly desirable for such substances not to trigger any skin irritation. The selection of such substances known in the prior art is limited. One object of the present invention was therefore to enrich the art in this respect.

The present invention relates, in addition, to antioxidants, preferably those which are employed in cosmetic or dermatological skin-care preparations. The invention also relates, in particular, to cosmetic and dermatological preparations comprising such antioxidants. In a preferred embodiment, the present invention relates to cosmetic and dermatological preparations for the prophylaxis and treatment of cosmetic or dermatological cell alterations, especially skin alterations such as, for example, skin ageing, and in particular cell ageing, especially skin ageing, which is induced by oxidative processes.

The damaging effect of the ultraviolet component of solar radiation on the skin is widely known. Whereas rays with a wavelength of less than 290 nm (the so-called UVC range) are absorbed by the ozone layer in the earth's atmosphere, rays in the range between 290 nm and 320 nm, the so-called UVB range, are the cause of erythema, simple sunburn or even more or less severe burns.

The lower range of sunlight around 308 nm is said to show maximum erythemal activity.

Numerous compounds are known for protection against UVB radiation, these compounds being derivatives of 3-benzylidenecamphor, of 4-aminobenzoic acid, of cinnamic acid, of salicylic acid, of benzophenone and also of 2-phenylbenzimidazole.

For the range between about 320 nm and about 400 nm, the so-called UVA range, it is also important to have filter substances available, since rays in this range can give rise to reactions on light-sensitive skin. It has been shown that UVA radiation leads to damage to the elastic and collagenic fibres of connective tissue, causing the skin to age prematurely, and that this radiation is to be regarded as a cause of numerous phototoxiic and photoallergic reactions. The damaging effect of UVB radiation can be intensified by UVA radiation.

Therefore, to protect against the rays of the UVA range, certain derivatives of dibenzoylmethane are used.

However, UV radiation can also lead to photochemical reactions, in which case the photochemical reaction products then intervene in skin metabolism.

Photochemical reaction products of this kind are chiefly free-radical compounds, for example hydroxyl radicals. Undefined free-radical photo-products which are formed in the skin itself can also, because of their high reactivity, show uncontrolled secondary reactions. And singlet oxygen, a nonradical excited state of the oxygen molecule, can occur under UV radiation, as can short-lived epoxides and many others. Singlet oxygen, for example, is distinguished from the triplet oxygen normally present (free-radical ground state) by heightened reactivity. Nevertheless, excited reactive (free-radical) triplet states of the oxygen molecule also exist.

Furthermore, UV radiation is counted among ionizing radiation. There is therefore the risk of ionic species being formed during UV exposure, which then in turn are capable of oxidative intervention in biochemical processes.

To prevent these reactions, additional antioxidants and/or free-radical scavengers can be incorporated into the cosmetic and/or dermatological formulations.

It has already been proposed to employ vitamin E, a substance of known antioxidative action, in light-protection formulations, although here too the effect achieved falls far short of that hoped for.

In past years, many different derivatives and administration forms of vitamin E have been developed in order to increase its availability. Such derivatives are often tocopheryl esters which, however, have the disadvantage that their antioxidative activity is markedly lower than that of nonderivatized vitamin E. Moreover, such derivatives are usually soluble only in fats or organic solvents. Tocopheryl phosphates and tocopheryl ethoxylates, which are synthetically accessible, have other disadvantages.

One object of the present invention was to develop tocopheryl derivatives having advantageous antioxidative properties and a favourable solubility for cosmetic and pharmaceutical formulation.

Another object of the invention was to provide cosmetic, dermatological and pharmaceutical active substances and preparations, and light-protection formulations, which serve for the prophylaxis and treatment of light-sensitive skin, especially of photodermatoses, preferably PPD.

Other terms for polymorphic photodermatosis are PPD, PLE, Mallorca acne and a large number of other terms as are given in the literature (e.g. A. Voelckel et al., Zentralblatt Haut- und Geschlechtskrankheiten (1989), 156, p.2).

The invention also relates to the mixtures of the active substances and preparations with them.

Furthermore, the present invention relates to active substances, and preparations comprising such active substances, for the cosmetic and dermatological treatment or prophylaxis of erythemal, inflammatory, allergic or autoimmune-reactive symptoms, especially dermatoses. The invention additionally relates to the use of such active substances, and of preparations comprising such active substances, for the immunostimulation of the skin, and advantageously in this context for immunostimulation with the effect of treating damaged skin, especially for the treatment of wounds.

As a barrier organ of the human organism, the skin, especially the epidermis, is particularly subject to external influences. According to current scientific understanding, the skin constitutes an immunological organ which, as an immunocompetent peripheral compartment, plays its own role in inductive, effective and regulatory immune processes of the overall organism.

The epidermis is richly equipped with nerves and peripheroceptors, such as Vater-Pacini lamellated corpuscles, Merkel cell-neurite complexes and free nerve endings for sensation of pain, cold and heat and itching.

Immunosuppression in general is the suppression or lessening of the reactivity of the immune system. Immunosuppression can be classified into local and systemic effects. Ultimately, it embraces a multiplicity widely varying aspects, all of which comprise a reduction in the normal immunological defence mechanisms of the skin.

Many more or less sensitive persons suffer erythemal skin phenomena even when using some preparations with a deodorant or antiperspirant action.

Erythemal skin phenomena also arise as concomitant symptoms with certain skin diseases or skin irregularities. For example, the typical skin eruption in the clinical picture of acne regularly shows severe reddening to a greater or lesser extent.

Antioxidants are predominantly used as substances for protection against the decay of the preparations comprising them. Neverthless, it is known that unwanted oxidation processes can also occur in human and animal skin. Such processes play an important role in skin ageing.

The paper "Skin Diseases Associated with Oxidative Injury" in "Oxidative Stress in Dermatology", p. 323 ff. (Marcel Decker Inc., New York, Basel, Hong Kong, editor: Jürgen Fuchs, Frankfurt, and Lester Packer, Berkeley, Calif.) details oxidative damage to the skin and the root causes of such damage.

If human hair is to be coloured permanently, only oxidizing hair-colouring methods are suitable in practice. During oxidative colouring of the hair, the dye chromophore is formed by reaction of precursors (phenols, aminophenols, and also—but less frequently—diamines) and bases (usually p-phenylenediamine) with the oxidizing agent, usually hydrogen peroxide. In such methods, hydrogen peroxide concentrations of around 6% are frequently employed.

It is usually assumed that, in addition to the colouring effect, a bleaching effect also occurs owing to the hydrogen peroxide. In oxidatively coloured human hair, as is the case with bleached hair, microscopic holes can be detected at the places where melanin granules were present.

The fact is that the oxidizing agent hydrogen peroxide can react not only with the dye precursors but also with the hair substance and, in doing so, can under certain circumstances cause damage to the hair.

Antioxidants are substances which prevent oxidation processes or which prevent the autoxidation of fats containing unsaturated compounds. Antioxidants used in the field of cosmetics and pharmaceuticals are, for example, α-tocopherol, especially in the form of α-tocopheryl acetate, sesame oil, bile acid derivatives, butylhydroxyanisole and butylated hydroxytoluene.

In order to prevent such reactions, antioxidants and/or free-radical scavengers can also be incorporated in addition into cosmetic formulations.

Indeed, some antioxidants and free-radical scavengers are known. Thus, U.S. Pat. Nos. 4,144,325 and 4,248,861 and numerous other documents have already proposed to employ vitamin E, a substance with a known antioxidative action, in light-protection formulations, but here too the effect achieved falls far short of that hoped for.

An object of the present invention was to eliminate the disadvantages of the prior art. In particular, the intention was to make available active substances, and preparations comprising such active substances, which, when used, are able at least to reduce, if not entirely to prevent, damage to the skin and/or hair caused by an oxidative effect.

A further object of the present invention was to provide cosmetic preparations which, before or after treatment of the hair with hair-colouring preparations, even those containing strong oxidizing agents such as hydrogen peroxide, counteract the damaging oxidation effect thereof.

The intention was in particular to provide active substances, and preparations comprising such active substances, for the cosmetic and dermatological treatment and/or prophylaxis of erythemal, inflammatory, allergic or autoimmune-reactive symptoms, especially dermatoses, but also the symptom of "stinging".

The intention was furthermore to provide those active substances, and preparations comprising such active substances, which can be used for the immunostimulation of the skin, and advantageously in this context for immunostimulation effecting action which promotes wound healing.

A final object of the present invention was to design preparation processes for these active substances.

It was surprising, and not foreseeable by the person skilled in the art, that tocopheryl glycosides of the general formula

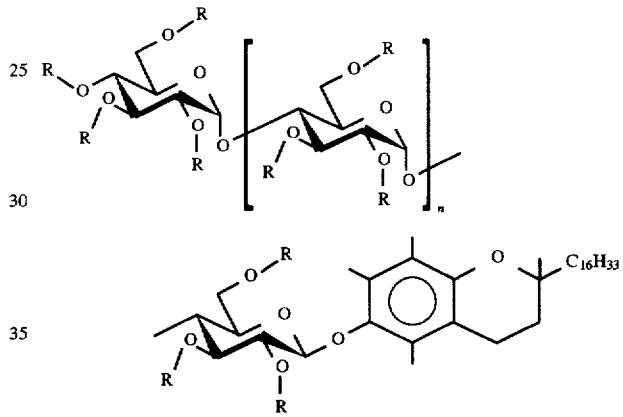

and/or of the general formula

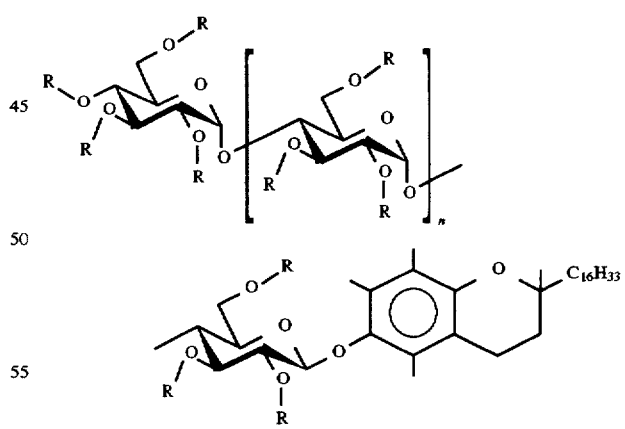

where n can adopt values of 0–6 and where R represents a radical from the group consisting of H, branched and unbranched alkyl of 1–18 carbon atoms, branched and unbranched acyl of 1–18 carbon atoms, and where R within one molecule can be identical in all positions of the glycosyl groups, but can also adapt different meanings within one molecule, such that it is possible within one molecule to choose any desired combinations of the radicals represented, eliminate all of the described disadvantages of the prior art.

In this context, it is advantageous to choose the tocopherol unit on which the tocopheryl glycosides according to the invention are based from all naturally occurring or synthetically accessible tocopherol structures. It is particularly advantageous in accordance with the invention to choose, as the basic tocopherol unit, DL-α-tocopherol in its naturally occurring configuration. It is especially advantageous for R to be H in all substitution positions.

The preferred compounds are named as follows:

n=0: tocopheryl β-D-maltoside and tocopheryl α-D-maltoside n=1: tocopheryl β-D-maltotrioside and tocopheryl α-D-maltotrioside n=2: tocopheryl β-D-maltotetraoside and tocopheryl α-D-maltotetraoside n=3: tocopheryl β-D-maltopentaoside and tocopheryl α-D-maltopentaoside n=4: tocopheryl β-D-maltohexaoside and tocopheryl α-D-maltohexaoside n=5: tocopheryl β-D-maltoheptaoside and tocopheryl α-D-maltoheptaoside n=6: tocopheryl β-D-maltooctaoside and tocopheryl α-D-maltooctaoside n=7: tocopheryl β-D-maltoenneaoside and tocopheryl α-D-maltoenneaoside n=8: tocopheryl β-D-maltodecaoside and tocopheryl α-D-maltodecaoside In general, both the tocopheryl α-glycosides and the tocopheryl β-glycosides can be used with advantage in accordance with the invention. The β-glycosides are particularly advantageous.

Mixtures of α- and β-glycosides can also be advantageous in accordance with the invention. In any case, the person skilled in the art is aware of a large number of methods capable of separating the anomers, such as chromatographic methods, for example.

It is particularly advantageous if n is 1. R is especially advantageously H in all substitution positions. Accordingly, the preferred tocopheryl derivative is represented by the structural formula It was therefore not foreseeable by the person skilled in the art that the tocopheryl glycosides according to the invention, and cosmetic or dermatological preparations comprising these glycosides, would act better as antioxidant act better as a free-radical scavenger better prevent the binding of harmful photo-products to lipids, DNA and proteins act better against skin ageing protect the skin better against photoreactions, especially PPD better prevent inflammatory reactions than the active substances, active-substance combinations and preparations of the prior art, and, furthermore possess good dispersibility or solubility in water exhibit exemplary surfactant properties increase the moisture level of the skin in an astonishing manner.

The tocopheryl derivatives according to the invention are capable of minimizing the damaging effects of oxygen on the human skin, even under the simultaneous influence of ultraviolet light.

The invention therefore relates to the use of the tocopheryl glycosides according to the invention as antioxidants and to their use for the combating and/or prophylaxis of skin ageing and inflammatory reactions induced by oxidative attack.

The invention also relates to processes for the preparation of tocopheryl glycosides according to the invention, characterized in that an oligosaccharide or an oligosaccharide derivative of the general formula

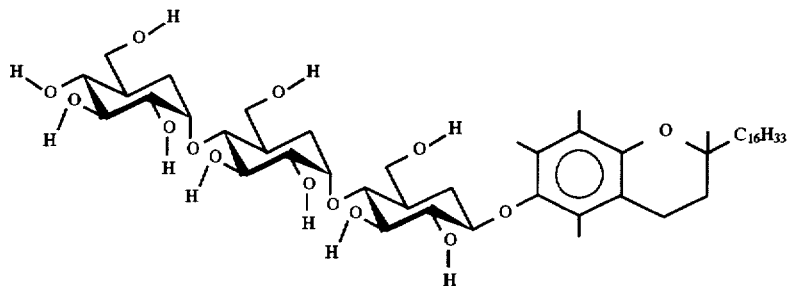

The $C_{16}H_{33}$ radical is represented by the structural formula

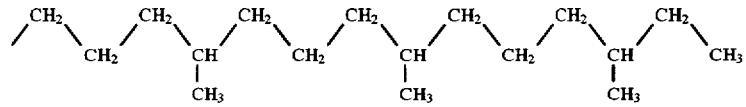

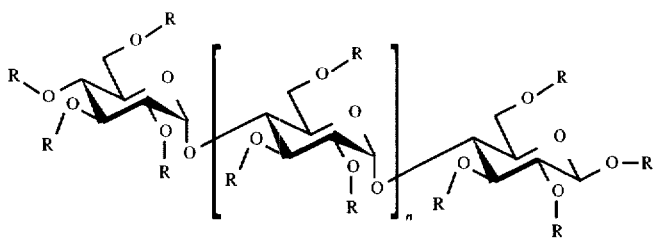

and/or an oligosaccharide or an oligosaccharide derivative of the general formula

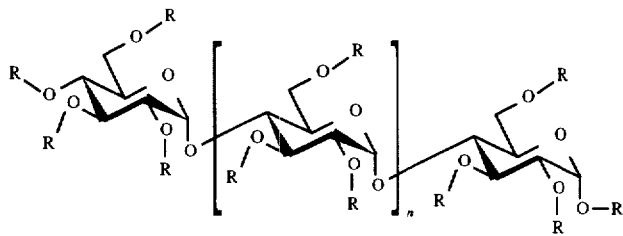

where n can adopt values of 0–6 and where R represents a radical from the group consisting of H, branched and unbranched alkyl of 1–18 carbon atoms, branched and unbranched acyl of 1–18 carbon atoms, and where R within one molecule can be identical in all positions of the glycosyl groups, but can also adopt different meanings within one molecule, such that it is possible within one molecule to choose any desired combinations of the radicals represented, are combined with a tocopherol derivative of the general formula

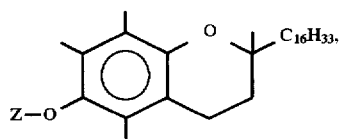

where Z is preferably a hydrogen atom, and, if desired, a protolysis step takes place such that one or more radicals R which are not H is or are exchanged for H by means of this protolysis step.

Preference is given to a process for the preparation of tocopheryl glycosides according to the invention, characterized in that the oligosaccharide or the oligosaccharide derivative and the tocopherol derivative react with one another in the presence of a Lewis acid.

Particular preference is given to a process for the preparation of tocopherol glycosides according to the invention, characterized in that the Lewis acid is chosen from the group consisting of $BF_3.Et_2O$, $SnCl_4$ and $ZnCl_2$.

If it is desired to carry out a protolysis step such that one or more radicals R which are not E is or are exchanged for H by means of this protolysis step, it is advantageous if the protolysis step consists in adding a proton donor and a basic agent.

In this case, it is preferred that the basic agent is chosen from the group consisting of alkali metal alkanolates, alkali metal carbonates and amines.

The preparation of the tocopheryl glycosides according to the invention is preferably carried out in accordance with the reaction scheme

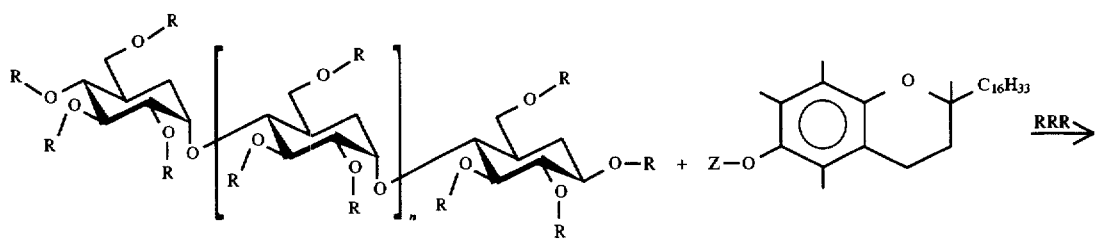

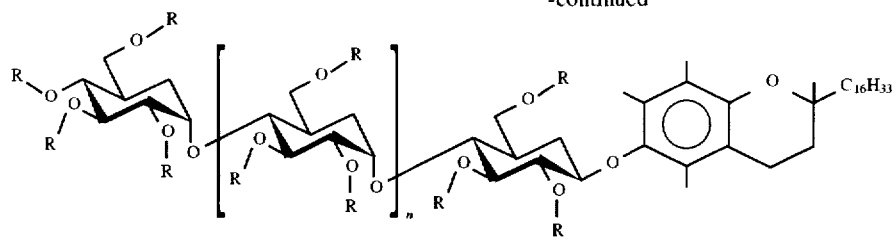

The radical Z is advantageously hydrogen. In this reaction, the reaction conditions RRR can, in principle, be taken from the store of knowledge familiar to the person skilled in the art. However, it is advantageous and based on independent inventive effort to observe the conditions which are disclosed herein.

The above scheme shows the synthesis of a β-glycoside. The synthesis of an α-glycoside is advantageously carried out in accordance with the reaction scheme If R=H, it is advantageous to provide the OH groups, prior to the coupling of the tocopheryl radical with the oligoglycoside, with protecting groups, which are designated in the structural formulae and reaction schemes by the abbreviation "PG":

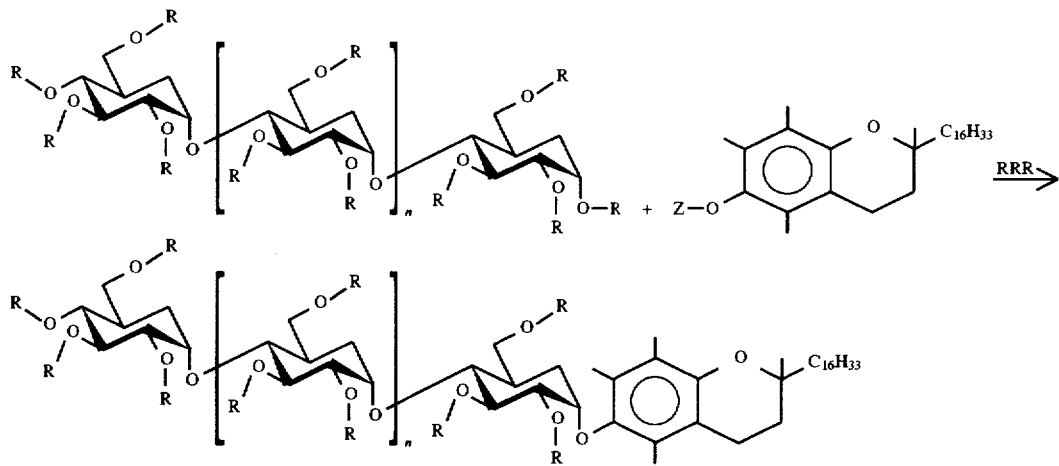

The reaction conditions correspond, mutatis mutandis, to those for the corresponding β-glycosides.

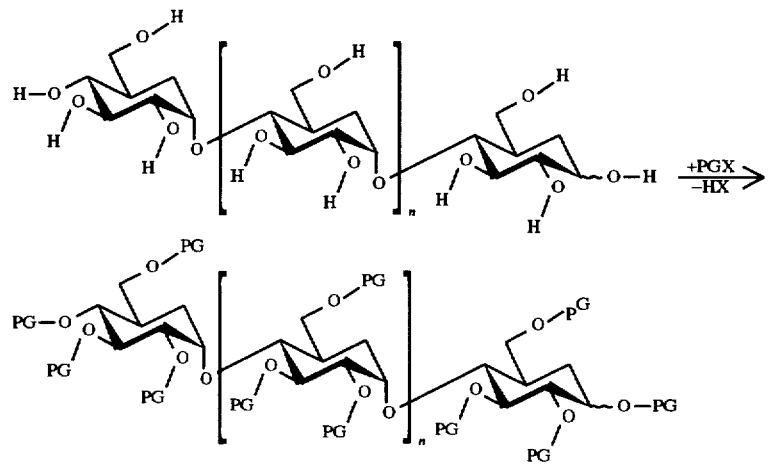

Such a procedure is very familiar in principle to the person skilled in the art. However, it has been found advantageous to protect the OH groups of the oligoglycosides on which the tocopheryl glycosides according to the invention are based with acetyl radicals. This can be carried out, for example, by heating the oligoglycoside with acetic anhydride and, if desired, sodium acetate and/or zinc chloride, typically over periods ranging from a few minutes to several hours, for example at 120° C. for 2 hours. With this reaction regime, from an anomer mixture, the acetyl β-glycoside is formed predominantly:

organic solvents such as, for example, dichloromethane. It is advantageous to carry out the reaction in the temperature range of 0° C.–50° C., preferably at room temperature. It can be advantageous to operate with the exclusion of light.

It is of course clear to the person skilled in the art that the corresponding tocopheryl α-glycoside can be produced from the appropriate glycoside with the acetate radical in the α position.

Furthermore, it is advantageous to perform the glycosidation under substantial, and preferably complete, exclusion of oxygen and other oxidizing agents.

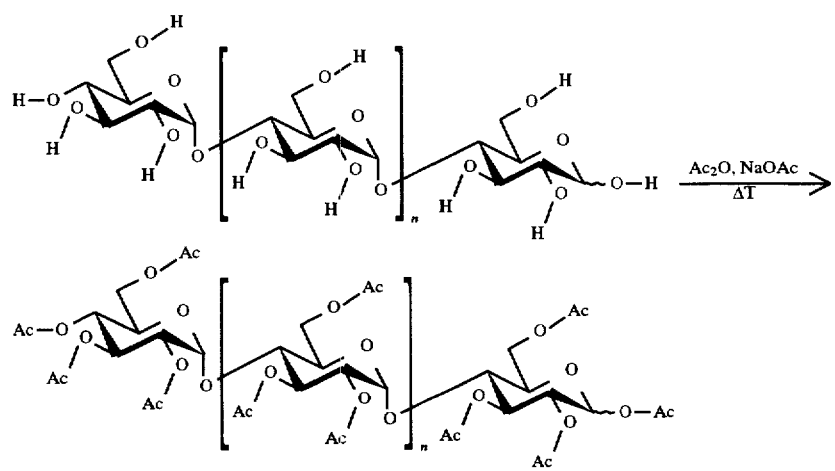

The oligoglycoside protected in this way can then, using customary glycosidation auxiliaries, be united with the tocopherol parent structure. Glycosidation agents which have been found to be advantageous are Lewis acids, especially $BF_3 \cdot Et_2O$. $SnCl_4$ and/or $ZnCl_2$ can also be used with advantage.

Accordingly, the preferred reaction scheme in

However, it is also advantageous to choose different glycosidation conditions. For example, enzymatic processes can be employed. The process described in JP-A Sho-60-56994 has also proved to be favourable.

Where the protecting groups are to be eliminated, the customary auxiliaries are available to the person skilled in the art. For example, it is advantageous to eliminate acetyl

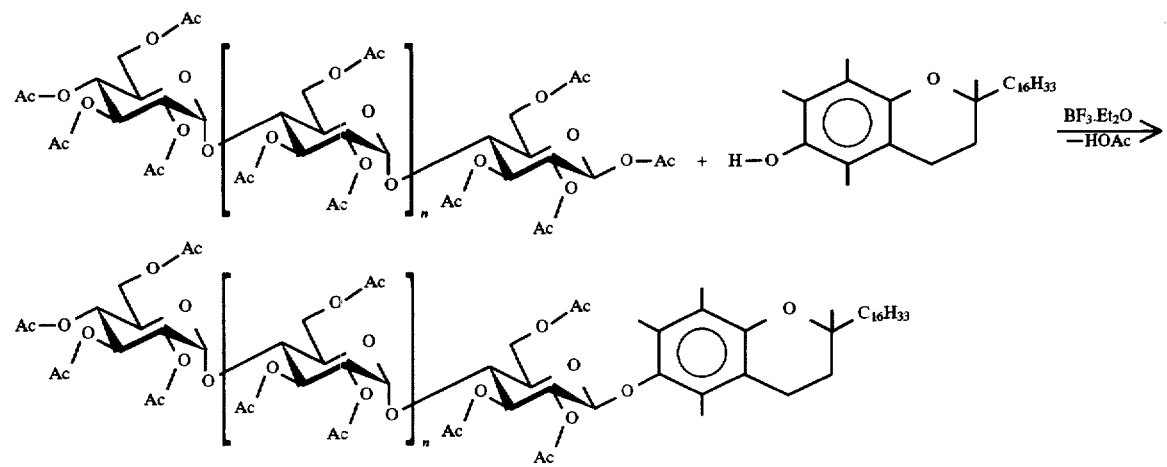

60

The above reaction advantageously takes place with at least substantial, and preferably complete, exclusion of water in groups in a basic medium, for instance in accordance with the reaction scheme:

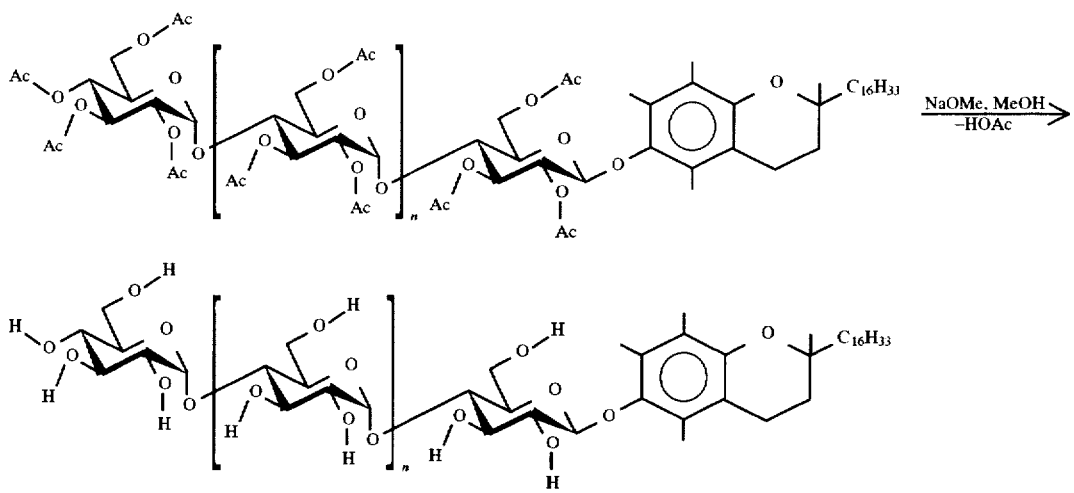

As in the above scheme, alkali metal alcoholates can be used as bases, as can weaker bases such as $K_2CO_3$. It is also advantageous to carry out the elimination of the protecting groups in a medium comprising triethylamine, methanol and water, preferably in a ratio of about 1:8:1.

The cosmetic or dermatological formulations according to the invention can have the customary composition and can be used for the treatment, care and cleansing of the skin and/or hair and as a make-up product in decorative cosmetics. They preferably contain from 0.001% by weight to 10% by weight, but in particular from 0.01% by weight to 6% by weight, based on the overall weight of the composition, of the tocopheryl glycosides according to the invention.

For use, the cosmetic and dermatological preparations according to the invention are applied, in the manner customary for cosmetics, to the skin and/or the hair in a sufficient quantity.

Cosmetic and dermatological preparations according to the invention can be in various forms. For example, they can constitute a solution, a nonaqueous preparation, an emulsion or microemulsion of the water-in-oil (W/O) type or of the oil-in-water (O/W) type, a multiple emulsion, for example of the water-in-oil-in-water (W/O/W) type, a gel, a solid stick, an ointment or else an aerosol. It is also advantageous to administer the tocopheryl glycosides according to the invention in encapsulated form, for example in collagen matrices and other usual encapsulating materials, for example as cellulose capsules, and encapsulated in gelatin, wax matrices or liposomally. Wax matrices as are described in DE-A 43 08 282 have been found to be particularly favourable.

It is also possible and advantageous in the context of the present invention to introduce the tocopheryl glycosides according to the invention into aqueous systems or surfactant preparations for cleansing the skin and hair.

It is therefore also regarded as an advantageous embodiment of the present invention to provide for the use of tocopheryl glycosides according to the invention for protection of the skin and/or hair against exposure to oxidation, especially this use of the tocopheryl glycosides according to the invention in shampoos and washing formulations.

The cosmetic and dermatological preparations according to the invention can comprise cosmetic auxiliaries such as are usually used in such preparations, for example preservatives, bactericides, fragrances, substances for preventing foaming, dyes, pigments which have a colouring effect, thickeners, surface-active substances, emulsifiers, softening, moisturizing and/or humectant substances, fats, oils, waxes or other customary constituents of a cosmetic or dermatological formulation, such as alcohols, polyols, polymers, foam stabilizers, electrolytes, organic solvents or silicone derivatives.

In particular, the tocopheryl glycosides according to the invention can also be combined with other antioxidants.

Favourable antioxidants which can be used in accordance with the invention are all antioxidants which are suitable or customary for cosmetic and/or dermatological applications.

The antioxidants are advantageously chosen from the group consisting of amino acids (for example glycine, histidine, tyrosine and tryptophan) and derivatives thereof, imidazoles (for example urocanin acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, chlorogenic acid and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodidipropionate, distearyl thiodipropionate, thiodipropionic acid and derivatives thereof (esters, ethers, peptides, lipids, nucleotides, nucelosides and salts) and sulphoximine compounds (for example buthionine-sulphoximines, homocysteine-sulphoximine, buthionine sulphones and penta-, hexa- and heptathioninesulphoximine) in very low tolerated dosages (for example pmol to µmol/kg), and also (metal) chelating agents (for example α-hydroxy fatty acids, palmitic acid, phytic acid and lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, ubiquinone and ubiquinol and derivatives thereof, vitamin C and derivatives (for example ascorbyl palpitate, Mg ascorbyl phosphate, ascorbyl acetate), tocopherols and derivatives (for example vitamin E acetate), vitamin A and derivatives (vitamin A palpitate) and coniferyl benzoate of benzoin resin, rutic acid and derivatives thereof, α-glycosylrutin, ferulic acid, furfurylideneglucitol, carnosine, butylated hydroxytoluene, butylhydroxyanisole, nordihydroguaic resin acid, nordihydroguaiaretic acid, trihydroxybutyrophenone, uric acid and derivatives thereof, mannose and derivatives thereof, zinc and derivatives thereof (for example ZnO, ZnSO$_4$), selenium and derivatives thereof (for example selenium-methionine), stilbenes and derivatives thereof (for example stilbene oxide, trans-stilbene oxide) and those derivatives (salts, esters, ethers, sugars, nucleotides, nucleosides, peptides and lipids) of these abovementioned active substances which are suitable in accordance with the invention.

The quantity of the abovementioned antioxidants (one or more compounds) which are not identical with the tocopheryl glycosides according to the invention in the preparations is preferably from 0.001 to 30% by weight, particularly preferably 0.05–20% by weight, in particular 1–10% by weight, based on the overall weight of the preparation.

If vitamin E and/or derivatives thereof constitute the antioxidant or antioxidants, it is advantageous to choose their respective concentrations from the range of 0.001–10% by weight, based on the overall weight of the formulation.

If vitamin A or vitamin A derivatives, or carotenes or their derivatives, constitute the antioxidant or antioxidants, it is advantageous to choose their respective concentrations from the range of 0.001–10% by weight, based on the overall weight of the formulation.

Emulsions according to the invention are advantageous and comprise, for example, the fats, oils, waxes and other fatty substances mentioned, as well as water and an emulsifier as is customarily used for a formulation of this type.

In this case, the lipid phase can advantageously be chosen from the following group of substances:

- naturally occurring, synthetic and/or semisynthetic oils, such as triglycerides of capric or caprylic acid, but preferably castor oil;
- fats, waxes and other naturally occurring, synthetic and/or semisynthetic fatty substances, preferably esters of fatty acids with alcohols of low carbon number, for example with isopropanol, propylene glycol or glycerol, or esters of fatty alcohols with alkanoic acids of low carbon number or with fatty acids;
- silicone oils such as dimethylpolysiloxanes, diethylpolysiloxanes, diphenylpolysiloxanes and mixed forms thereof; and
- saturated compounds such as hydrocarbons of natural or synthetic origin (vaseline, squalane).

The aqueous phase of the preparations according to the invention advantageously comprises, where appropriate, alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products and also, in particular, one or more thickeners, which can advantageously be chosen from the group consisting of silica, aluminium silicates, polysaccharides and/or derivatives thereof, for example hyaluronic acid, xanthan gum, hydroxypropylmethylcellulose, and with particular advantage from the group consisting of the polyacrylates, preferably a polyacrylate from the group consisting of the so-called Carbopols, for example Carbopols of types 980, 981, 1382, 2984, 5984, in each case individually or in combination.

Mixtures of the abovementioned solvents are used in particular. In the case of alcoholic solvents, water can be a further constituent.

Gels according to the invention usually comprise alcohols with low carbon number, for example ethanol, isopropanol, 1,2-propanediol, glycerol and water, or an abovementioned oil, in the presence of a thickener which in the case of oily-alcoholic gels is preferably silica or an aluminium silicate and in the case of aqueous-alcoholic or alcoholic gels is preferably a polyacrylate.

Suitable propellants for preparations according to the invention which can be sprayed from aerosol containers are the customary known readily volatile, liquefied propellants, for example hydrocarbons (propane, butane, isobutane), which can be employed by themselves or as a mixture with one another. Compressed air can also advantageously be used.

Preparations according to the invention can, furthermore, advantageously comprise substances which absorb UV radiation in the UVB region, the overall quantity of filter substances being, for example, from 0.1% by weight to 30% by weight, preferably from 0.5 to 10% by weight, in particular from 1.0 to 6.0% by weight, based on the overall weight of the preparations, in order to provide cosmetic preparations which protect the hair or skin from the entire range of ultraviolet radiation. They can also be used as sunscreens for the hair or skin.

Where the emulsions according to the invention comprise UVB filter substances, they can be oil-soluble or water-soluble. Examples of oil-soluble UVB filters which are advantageous according to the invention are:

- 3-benzylidenecamphor derivatives, preferably 3-(4-methylbenzylidene)camphor, 3-benzylidenecamphor;
- 4-aminobenzoic acid derivatives, preferably 2-ethylhexyl 4-(dimethylamino)benzoate and amyl 4-(dimethylamino)benzoate;
- esters of cinnamic acid, preferably 2-ethylhexyl 4-methoxycinnamate and isopentyl 4-methoxycinnamate;
- esters of salicylic acid, preferably 2-ethylhexyl salicylate, 4-isopropylbenzyl salicylate and homomenthyl salicylate;
- derivatives of benzophenone, preferably 2-hydroxy-4-methoxybenzophenone, 2-hydroxy-4-methoxy-4'-methyl-benzophenone and 2,2'-dihydroxy-4-methoxybenzophenone; and
- esters of benzalmalonic acid, preferably di(2-ethylhexyl) 4-methoxybenzalmalonate;
- 2,4,6-trianilino(p-carbo-2'-ethyl-1'-hexyloxy)-1,3,5-triazine.

Examples of advantageous water-soluble UVB filters are:

- salts of 2-phenylbenzimidazole-5-sulphonic acid, such as its sodium, potassium or triethanol ammonium salt, and the sulphonic acid itself;
- sulphonic acid derivatives of benzophenones, preferably 2-hydroxy-4-methoxybenzophenone-5-sulphonic acid and salts thereof;
- sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)sulphonic acid and salts thereof.

The list of the UVB filters mentioned which can be used in combination with the tocopheryl glycosides according to the invention is, of course, not intended to be limiting.

The invention also relates to the use of a combination of the tocopheryl glycosides according to the invention with at least one UVB filter as an antioxidant and to the use of a combination of the tocopheryl glycosides according to the invention with at least one UVB filter as an antioxidant in a cosmetic or dermatological preparation.

It can also be advantageous to combine tocopheryl glycosides according to the invention with UVA filters which have customarily been present to date in cosmetic preparations. These substances are preferably derivatives of dibenzoylmethane, especially 1-(4'-tert-butylphenyl)-3-(4-methoxyphenyl)propane-1,3-dione and 1-phenyl-3-(4'-isopropylphenyl)propane-1,3-dione. The invention additionally relates to these combinations and to preparations which comprise these combinations. The quantities used for the UVB combination can be employed.

The invention also relates to the use of a combination of the tocopheryl glycosides according to the invention with at least one UVA filter as an antioxidant and to the use of a combination of the tocopheryl glycosides according to the invention with at least one UVA filter as an antioxidant in a cosmetic or dermatological preparation.

The invention also relates to the use of a combination of the tocopheryl glycosides according to the invention with at least one UVA filter and at least one UVB filter as an antioxidant and to the use of a combination of the tocopheryl glycosides according to the invention with at least one UVA filter and at least UVB filter as an antioxidant in a cosmetic or dermatological preparation.

Cosmetic and dermatological preparations having an active content of tocopheryl glycosides according to the invention can also comprise inorganic pigments which are customarily used in cosmetics for protecting the skin against UV rays. These pigments are oxides of titanium, zinc, iron, zirconium, silicon, manganese and aluminium, cerium and mixtures thereof, and modifications in which the oxides are the active agents. The pigments are particularly preferably those based on titanium dioxide.

The invention additionally relates to these combinations of UVA filter and pigment and to preparations which comprise these combinations. The quantities mentioned for the above combinations can be employed.

Cosmetic and dermatological preparations for protecting the hair against UV rays in accordance with the invention are, for example, shampooing compositions, preparations which are used when rinsing the hair before or after shampooing, before or after permanent waving or before or after colouring or bleaching the hair, preparations for blow-drying or setting the hair, preparations for colouring or bleaching, a styling and treatment lotion, a hair lacquer or perming compositions.

The cosmetic and dermatological formulations comprise active substances and auxiliaries such as are customarily employed for this type of preparation for hair care and hair treatment. Auxiliaries used are preservatives, surface-active substances, substances for preventing foaming, thickeners, emulsifiers, fats, oils, waxes, organic solvents, bactericides, fragrances, dyes or pigments, the function of which is to colour the hair or the cosmetic or dermatological preparation itself, electrolytes and substances to prevent the hair from becoming greasy.

The term electrolytes in the context of the present invention refers to water-soluble alkali metal, ammonium, alkaline earth metal (including magnesium) and zinc salts of inorganic anions and any desired mixtures of such salts, it being necessary to ensure that these salts are distinguished by pharmaceutical or cosmetic acceptability.

The anions according to the invention are preferably chosen from the group consisting of chlorides, sulphates and hydrogen sulphates, phosphates, hydrogen phosphates and linear and cyclic oligophosphates, and also carbonates and hydrogen carbonates.

Cosmetic preparations which constitute a skin cleansing composition or shampooing composition preferably comprise at least one anionic, nonionic or amphoteric surface-active substance, or else mixtures of such substances, tocopheryl glycosides according to the invention in an aqueous medium, and auxiliaries such as are usually used for this purpose. The surface-active substance or the mixtures of these substances can be present in the shampooing composition in a concentration of between 1% by weight and 50% by weight.

Where the cosmetic or dermatological preparations are in the form of a lotion which is rinsed out and is employed, for example, before or after bleaching, before or after shampooing, between two shampooing steps, or before or after permanent waving, these lotions are, for example, aqueous or aqueous-alcoholic solutions which if desired comprise surface-active substances, the concentration of which can be between 0.1 and 10% by weight, preferably between 0.2 and 5% by weight.

These cosmetic or dermatological preparations can also be aerosols with the auxiliaries usually used for this purpose.

A cosmetic preparation in the form of a lotion which is not rinsed out, in particular a lotion for setting the hair, a lotion used for blow-drying the hair or a styling and treatment lotion, is in general an aqueous, alcoholic or aqueous-alcoholic solution and comprises at least one cationic, anionic, nonionic or amphoteric polymer or else mixtures thereof, as well as active-substance combinations according to the invention in an effective concentration. The quantity of polymers used is, for example, between 0.1 and 10% by weight, preferably between 0.1 and 3% by weight.

Cosmetic preparations for the treatment and care of the hair which comprise tocopheryl glycosides according to the invention can be in the form of emulsions of the nonionic or anionic type. In addition to water, nonionic emulsions comprise oils or fatty alcohols which, for example, can also be polyethoxylated or polypropoxylated, or else mixtures of the two organic components. If desired, these emulsions comprise cationic surface-active substances.

In accordance with the invention, cosmetic preparations for the treatment and care of the hair can be in the form of gels which, in addition to an effective content of tocopheryl glycosides according to the invention and solvents customarily used for this purpose, preferably water, also comprise organic thickeners, for example gum arabic, xanthan gum, sodium alginate, cellulose derivatives, preferably methyl cellulose, hydroxymethylcellulose hydroxyethylcellulose, hydroxypropylcellulose, hydroxypropylmethylcellulose or inorganic thickeners, for example aluminium silicates such as bentonites, for example, or a mixture of polyethylene glycol and polyethylene glycol stearate or distearate. The thickener is present in the gel, for example, in a quantity of between 0.1 and 30% by weight, preferably between 0.5 and 15% by weight.

The quantity of tocopheryl glycosides according to the invention in a composition intended for the hair is preferably from 0.05% by weight to 10% by weight, in particular from 0.5% by weight to 5% by weight, based on the overall weight of the composition.

Aqueous cosmetic cleansing compositions according to the invention or concentrated cleansing compositions of low or zero water content which are intended for aqueous cleansing can comprise anionic, nonionic and/or amphoteric surfactants, examples being conventional soaps, for example sodium salts of fatty acids, alkyl sulphates, alkyl ether sulphates and alkane- and alkylbenzenesulphonates sulphoacetates sulphobetaines
sarcosinates
amidosulphobetaines
sulphosuccinates
sulphosuccinic monoesters
alkyl ether carboxylates
protein-fatty acid condensates
alkylbetaines and amidobetaines
fatty acid alkanolamides
polyglycol ether derivatives Cosmetic preparations which constitute cosmetic cleansing preparations for the skin can be in liquid or solid form. In addition to tocopheryl glycosides according to the invention, they preferably comprise at least one anionic, nonionic or amphoteric surface-active substance or mixtures thereof, if desired one or more electrolytes and auxiliaries as are customarily used for this purpose. The surface-active substance can be present in the cleansing preparations in a concentration of between 1 and 94% by weight, based on the overall weight of the preparations.

Cosmetic preparations which constitute a shampooing composition comprise, in addition to an effective content of tocopheryl glycosides according to the invention, preferably at least one anionic, nonionic or amphoteric surface-active substance or mixtures thereof, if desired an electrolyte according to the invention and auxiliaries as are customarily used for this purpose. The surface-active substance can be present in the shampooing composition in a concentration of between 1% by weight and 94% by weight.

In addition to the abovementioned surfactants, the compositions according to the invention comprise water and, if desired, the additives customary in cosmetics, for example fragrance, thickener, colourants, deodorants, antimicrobial substances, agents which restore oils, complexing agents and sequestering agents, pearlescent agents, plant extracts, vitamins, active substances and the like.

The present invention also relates to a cosmetic method of protecting the skin and hair against oxidative and/or photooxidative processes, which is characterized in that a cosmetic composition comprising an effective concentration of tocopheryl glycosides according to the invention is applied to the skin or hair in a sufficient quantity.

The present invention likewise embraces a method of protecting cosmetic or dermatological preparations against oxidation or photooxidation, these preparations being, for example, preparations for the treatment and care of the hair, especially hair colouring compositions, hair lacquers, shampooing compositions and colour shampooing compositions, and also make-up products such as, for example, nail varnishes, lipsticks, complexion foundations, washing and shower preparations, creams for the treatment and care of the skin or any other cosmetic preparations whose constituents may be subject to stability problems during storage owing to oxidation and/or photooxidation, characterized in that the cosmetic preparations have an effective content of tocopheryl glycosides according to the invention.

The quantity of tocopheryl glycosides according to the invention in these preparations is preferably from 0.001% by weight to 10% by weight, in particular from 0.1% by weight to 3% by weight, based on the overall weight of the preparations.

The invention additionally relates to the process for the production of the cosmetic compositions according to the invention which is characterized in that tocopheryl glycosides according to the invention are incorporated in a manner known per se into cosmetic and dermatological formulations.

The examples which follow are intended to illustrate the present invention without limiting it. The preparation, which is illustrated in Examples 1–3, of the peracetates of the oligosaccharides, of the peracetates of the tocopheryl glycosides and, finally, of the tocopheryl glycosides themselves can be applied, mutatis mutandis, to all tocopheryl glycosides according to the invention and their precursors.

EXAMPLE 1

Acetylation: 1 mmol of maltotriose is added to a suspension, heated to 120° C., of 2 mmol of sodium acetate and acetic anhydride (per mmol of OH group of the maltotriose: 4 mmol of acetic anhydride). The temperature of the reaction mixture is held at about 120° C. for about 2 hours. Ice-water is then added (to 10 ml) to the reaction mixture for hydrolysis of the acetic anhydride. 3 mmol of dichloromethane are added and the mixture is stirred at room temperature for 12 hours. The aqueous phase is separated off and subjected three times to extraction with 10 mmol of dichloromethane each time. The combined organic phases are neutralized with saturated sodium hydroxide solution, washed twice with 10 ml of water and dried over magnesium sulphate. The solvent is removed in vacuo. Yield: 80% maltotriose peracetate.

EXAMPLE 2

0.6 mmol of the maltotriose peracetate obtained according to Example 1 and 3.6 mmol of α-tocopherol are dissolved with 1.44 mmol of $BF_3.Et_2O$ in anhydrous dichloromethane and the solution is stirred at room temperature with the exclusion of light. The reaction is terminated after three hours. The reaction mixture is neutralized with saturated sodium hydrogen carbonate solution, washed three times with water and dried over magnesium sulphate. The solvent is removed in vacuo. Purification by flash chromatography (eluent:dichloromethane/acetone in a ratio of 17:1) gives a yellowish glass-like substance. Yield: 69% peracetylated tocopheryl maltotrioside.

EXAMPLE 3

0.121 mmol of the peracetylated tocopheryl maltotrioside obtained in Example 2 are dissolved in oxygen-free absolute methanol to which freshly prepared sodium methanolate has been added in an amount sufficient to give a pH of 8. After complete reaction, the mixture is neutralized with ion exchanger (Amberlite 120 $H^+$). The reaction solution is concentrated under reduced pressure in a rotary evaporator and the residue is dried in vacuo. Yield: 77% tocopheryl β-D-maltotrioside.

EXAMPLE 4

| W/O emulsion | % by weight |
| --- | --- |
| DL-α-tocopheryl β-D-maltotrioside | 2.00 |
| polyglyceryl 3-diisostearate | 2.50 |
| paraffin wax | 3.00 |
| paraffin oil DAB [German Pharmacopoeia] 9 | 10.00 |
| cetearyl octanoate | 10.00 |
| beeswax | 4.00 |
| glycerol | 5.00 |
| fragrance, preservative, additives | q.s |
| demineralized water | ad100.00 |

EXAMPLE 5

| W/O emulsion | % by weight |
| --- | --- |
| DL-α-tocopheryl β-D-maltotrioside | 0.50 |
| DL-α-tocopheryl β-D-maltotetraoside | 0.50 |
| cholesterol | 1.50 |
| paraffin wax | 3.00 |
| vaseline | 5.00 |
| paraffin oil DAB 9 | 20.00 |
| glycerol | 5.00 |
| fragrance, preservative, additives | q.s. |
| water | ad100.00 |

EXAMPLE 6

| W/O emulsion | % by weight |
| --- | --- |
| DL-α-tocopheryl β-D-maltotrioside | 1.00 |
| cholesterol | 1.50 |
| paraffin wax | 3.00 |
| vaseline | 5.00 |
| paraffin oil DAB 9 | 20.00 |
| glycerol | 5.00 |
| fragrance, preservative, additives | q.s. |
| water | ad100.00 |

EXAMPLE 7

| W/O emulsion | % by weight |
| --- | --- |
| DL-α-tocopheryl β-D-maltotrioside | 0.50 |
| wool wax alcohols | 2.50 |
| paraffin wax | 6.00 |
| beeswax | 1.00 |
| vaseline | 3.00 |
| paraffin oil DAB 9 | 20.00 |
| glycerol | 5.00 |
| fragrance, preservative, additives | q.s. |
| water | ad100.00 |

EXAMPLE 8

| O/W emulsion | % by weight |
| --- | --- |
| DL-α-tocopheryl β-D-maltotetraoside | 1.00 |
| sorbitol stearate | 2.50 |
| vaseline | 2.50 |
| paraffin oil DAB 9 | 14.00 |
| hydrogenated coconut fatty acid glycerides | 1.00 |
| Carbomer 934 | 0.20 |
| 1,3-butylene glycol | 2.00 |
| fragrance, preservative, colourants, additives | q.s. |
| demineralized water | ad100.00 |

EXAMPLE 9

| O/W emulsion | % by weight |
| --- | --- |
| DL-α-tocopheryl β-D-maltohexaoside | 0.20 |
| glyceryl monostearate | 0.50 |
| stearic acid | 2.50 |
| vaseline | 3.00 |
| paraffin oil DAB 9 | 15.00 |
| Carbomer 934 | 0.20 |
| cetyl phosphate | 0.15 |

-continued

| O/W emulsion | % by weight |
| --- | --- |
| glycerol | 3.00 |
| dimethicone | 0.50 |
| fragrance, preservatives, colourants, additives | q.s. |
| deionized water | ad100.00 |

EXAMPLE 10

| O/W emulsion | % by weight |
| --- | --- |
| DL-α-tocopheryl β-D-maltohexaoside | 0.40 |
| glyceryl monostearate citrate | 1.00 |
| sorbitol stearate | 1.00 |
| vaseline | 1.00 |
| paraffin oil DAB 9 | 15.00 |
| hydrogenated coconut fatty acid glycerides | 1.00 |
| Carbomer 934 | 0.20 |
| cetyl phosphate | 0.10 |
| glycerol | 3.00 |
| fragrance, preservative, colourants, additives | q.s. |
| demineralized water | ad100.00 |

EXAMPLE 11

| O/W emulsion | % by weight |
| --- | --- |
| DL-α-tocopheryl β-D-maltotetraoside | 0.50 |
| glyceryl stearate citrate | 2.00 |
| vaseline | 4.00 |
| paraffin oil DAB 9 | 11.00 |
| hydrogenated coconut fatty acid glycerides | 3.00 |
| Carbomer 934 | 0.20 |
| glycerol | 3.00 |
| dimethicone | 1.00 |
| fragrance, preservative, colourants, additives | q.s. |
| demineralized water | ad100.00 |

EXAMPLE 12

| O/W emulsion | % by weight |
| --- | --- |
| DL-α-tocopheryl β-D-maltotetraoside | 1.00 |
| sorbitol stearate | 2.50 |
| vaseline | 2.50 |
| paraffin oil DAB 9 | 14.00 |
| hydrogenated coconut fatty acid glycerides | 1.00 |
| Carbomer 934 | 0.20 |
| cetyl phosphate | 0.15 |
| glycerol | 3.00 |
| 1,3-butylene glycol | 2.00 |
| octyl methoxycinnamate | 2.00 |
| fragrance, preservative, colourants, additives | q.s. |
| demineralized water | ad100.00 |

EXAMPLE 13

| O/W emulsion | % by weight |
| --- | --- |
| DL-α-tocopheryl β-D-maltotrioside | 0.50 |
| DL-α-tocopheryl β-D-maltotetraoside | 3.50 |
| DL-α-tocopheryl β-D-maltohexaoside | 0.50 |
| vaseline | 1.00 |
| paraffin oil DAB 9 | 15.00 |
| Carbomer 934 | 0.20 |
| cetyl phosphate | 0.15 |

| O/W emulsion | % by weight |
|---|---|
| glycerol | 5.00 |
| fragrance, preservative, colourants, additives | q.s. |
| demineralized water | ad 100.00 |

Using NaOH, the pH of the formulations specified in the examples, especially the O/W emuslions, can be adjusted advantageously to values in the range of 5.0–8.0.

We claim:

1. A method for the treatment of skin therapeutically to reduce alterations induced by oxidation processes which comprises applying thereto an amount effective therefor of tocopheryl glycosides of the formula

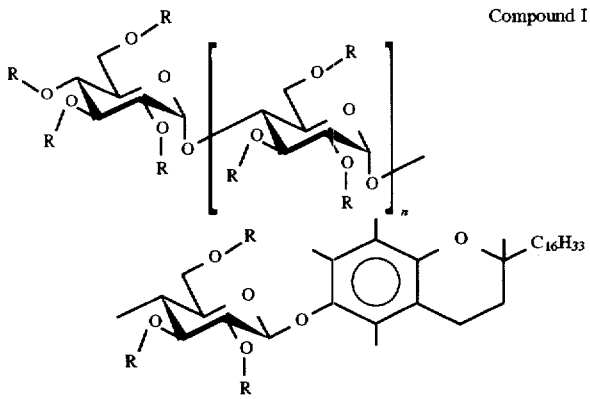

Compound I or of the formula

Compound II where n can adopt values of 0–8 and where R represents a radical selected from the group consisting of H, branched and unbranched alkyl of 1–18 carbon atoms, branched and unbranched acyl of 1–18 carbon atoms, and where R within one molecule can be identical in all positions of the glycosyl groups, but can also adopt different meanings within one molecule, such that it is possible within one molecule to choose any desired combinations of the radicals represented.

2. A method according to claim 1 wherein the tocopheryl glycosides are selected from the group consisting of tocopheryl β-D-maltoside, tocopheryl β-D-maltotrioside, tocopheryl β-D-maltotetraoside, tocopheryl β-D-maltopentaoside, tocopheryl β-D-maltohexaoside, tocopheryl β-D-maltoheptaoside, tocopheryl β-D-maltooctaosaide, tocopheryl β-D-maltoennneaoside and tocopheryl β-D-maltodecaoside.

3. A method according to claim 1, wherein said tocopheryl glycosides are prepared by reacting an oligosaccharide or an oligosaccharide derivative of the formula

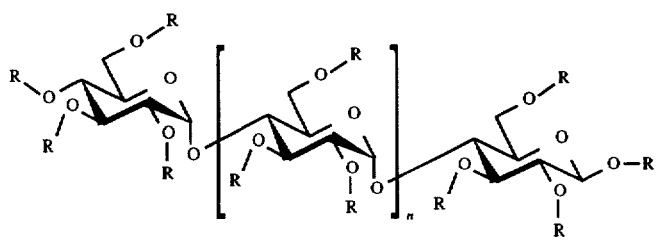

Compound III and/or an oligosaccharide or an oligosaccharide derivative of the formula

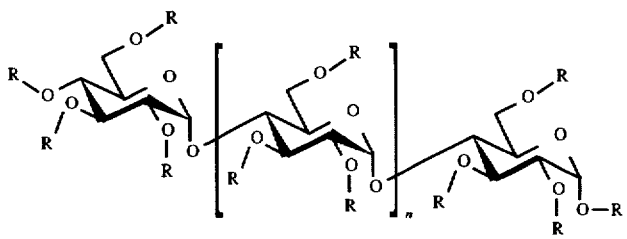

Compound IV where n can adopt values of 1–8 and where R represents a radical selected from the group consisting of H, branched and unbranched alkyl of 1–18 carbon atoms, branched and unbranched acyl of 1–18 carbon atoms, and where R within one molecule can be identical in all positions of the glycosyl groups, but can also adopt different meanings within one molecule, such that it is possible within one molecule to choose any desired combinations of the radicals represented, with a tocopherol derivative of the formula

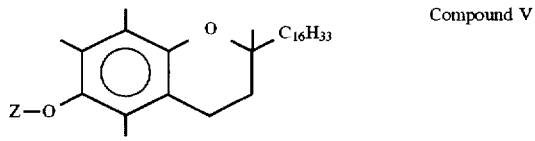

Compound V where Z is a moiety which as part of the tocopherol derivative as represented by Compound V reacts with a terminal OR group on the glycoside of Compounds III and IV to form the ether linkage of Compounds I and II between the glycoside and the tocopherol and, optionally a protolysis step wherein one or more radicals R which are not H is or are exchanged for H by means of this protolysis step.

4. A method according to claim 1, wherein the oligosaccharide or the oligosaccharide derivative and the tocopherol derivative react with one another in the presence of a Lewis acid.

5. A method according to claim 4, wherein the Lewis acid is selected from the group consisting of $BF_3.Et_2O$, $SnCl_4$ and $ZnCl_2$.

6. A method according to claim 1, wherein the protolysis step consists in adding a proton donor and a basic agent.

7. A method according to claim 6, wherein the basic agent is selected from the group consisting of alkali metal alkanolates, alkali metal carbonates and amines.

8. A method according to claim 3, wherein Z is hydrogen.

9. A method according to claim 1, wherein said tocopheryl glycosides are in the form of a composition including a cosmetically or pharmaceutically acceptable carrier.

* * * * *

UNITED STATES PATENT AND TRADEMARK OFFICE
CERTIFICATE OF CORRECTION

PATENT NO. : 5,780,445
DATED : July 14, 1998
INVENTOR(S) : Schneider, et al.

It is certified that error appears in the above-identified patent and that said Letters Patent is hereby corrected as shown below:

Title Page, item [57]; ABSTRACT: Line 11 delete " tie " and substitute -- the --

Signed and Sealed this

Twenty-second Day of February, 2000

Attest:

Q. TODD DICKINSON

Attesting Officer

Commissioner of Patents and Trademarks